(12) United States Patent
Cuschieri et al.

(10) Patent No.: US 9,801,655 B2
(45) Date of Patent: Oct. 31, 2017

(54) DEVICE FOR CREATING AN INTERCOSTAL TRANSCUTANEOUS ACCESS TO AN, IN PARTICULAR ENDOSCOPIC, OPERATING FIELD

(71) Applicant: University of Dundee, Dundee (GB)

(72) Inventors: Alfred Cuschieri, St. Andrews Fife (GB); Stuart Coleman, Dundee (GB); Duncan Martin, Dundee (GB)

(73) Assignee: University of Dundee, Dundee (GB)

( * ) Notice: Subject to any disclaimer, the term of this patent is extended or adjusted under 35 U.S.C. 154(b) by 476 days.

(21) Appl. No.: 14/484,988

(22) Filed: Sep. 12, 2014

(65) Prior Publication Data

US 2015/0080663 A1 Mar. 19, 2015

(30) Foreign Application Priority Data

Sep. 13, 2013 (EP) .................................... 13004464

(51) Int. Cl.
*A61B 17/34* (2006.01)
*A61B 17/02* (2006.01)

(52) U.S. Cl.
CPC ...... *A61B 17/3423* (2013.01); *A61B 17/0218* (2013.01); *A61B 17/0293* (2013.01); *A61B 17/0206* (2013.01); *A61B 2017/3419* (2013.01); *A61B 2017/3427* (2013.01); *A61B 2017/3445* (2013.01); *A61B 2017/3484* (2013.01); *A61B 2017/3488* (2013.01)

(58) Field of Classification Search
CPC .................. A61B 17/0293; A61B 2017/3427
See application file for complete search history.

(56) References Cited

U.S. PATENT DOCUMENTS

| | | | | |
|---|---|---|---|---|
| 4,130,113 A | * | 12/1978 | Graham | A61B 17/0293 600/224 |
| 5,776,110 A | | 7/1998 | Guy et al. | |
| 6,309,349 B1 | | 10/2001 | Bertolero et al. | |
| 8,403,840 B2 | * | 3/2013 | Wagner | A61B 17/0206 600/201 |
| 2007/0060939 A1 | * | 3/2007 | Lancial | A61B 1/00154 606/191 |
| 2011/0208006 A1 | | 8/2011 | Michaeli et al. | |
| 2015/0151093 A1 | * | 6/2015 | Rasulo | A61B 17/3417 606/186 |

FOREIGN PATENT DOCUMENTS

EP 2392275 A2 12/2011
EP 2601898 A2 6/2013

OTHER PUBLICATIONS

European Search Report Application No. EP13004464 dated Oct. 30, 2013; dated Nov. 7, 2013 pp. 6.

* cited by examiner

*Primary Examiner* — Andrew Yang
(74) *Attorney, Agent, or Firm* — Whitmyer IP Group LLC

(57) ABSTRACT

A device for creating an intercostal transcutaneous access to an, in particular endoscopic, operating field including a base body, which closely surrounds an incision all-side frame-shaped and with at least two webs mounted on the base body, which can be introduced into an intercostal space, by which two ribs arranged next to each other can be moved apart. To create a device for creating an intercostal transcutaneous access to an, in particular endoscopic, operating field which allows individual pressing apart of the ribs, it is proposed according to the invention that the at least two webs are mounted adjustable relative to each other on the base body.

14 Claims, 4 Drawing Sheets

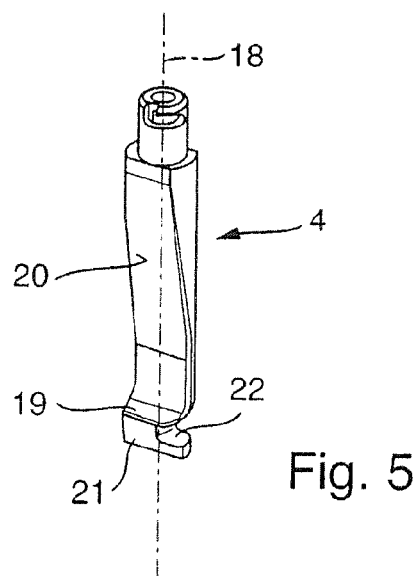
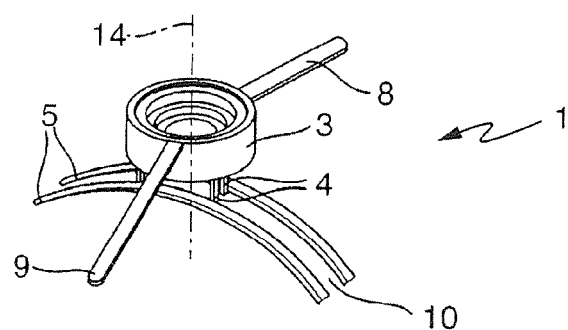
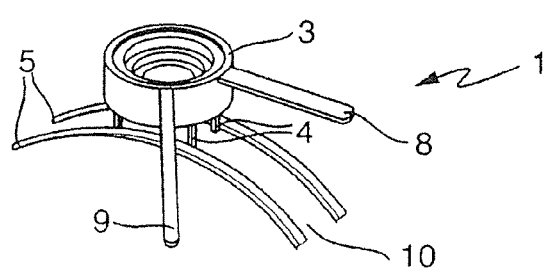
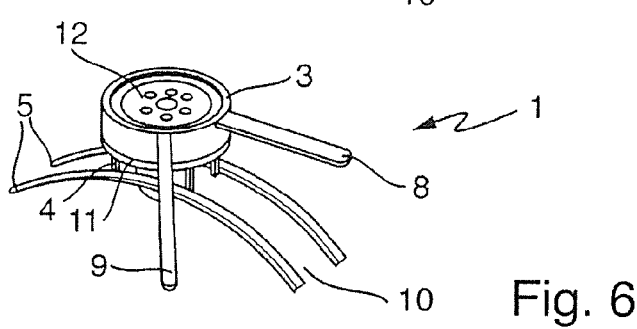
Fig. 5
Fig. 6

DEVICE FOR CREATING AN INTERCOSTAL TRANSCUTANEOUS ACCESS TO AN, IN PARTICULAR ENDOSCOPIC, OPERATING FIELD

FIELD OF THE INVENTION

The invention relates to a device for creating an intercostal transcutaneous access to an, in particular endoscopic, operating field comprising a base body, which closely surrounds an incision all-side frame-shaped and with at least two webs mounted on the base body, which can be introduced into an intercostal space, by which the two ribs arranged next to each other can be moved apart.

BACKGROUND OF THE INVENTION

During thoracic surgery it is necessary to gain access to the operating field intercostally, that is between the ribs of the patient. For open surgery a large incision is made and the operation is performed using clamps to pry the ribs apart, wherein it is not uncommon that the ribs break under the influence of such a spreading technique.

An alternative to the classic open surgery technique is minimal invasive thoracic endoscopy (thoracocscopy), for which a multiplicity of small access points are created between the ribs through which the endoscopic instruments can be guided into the operating field. However, the freedom of movement for the individual instruments is very limited due to the small clearances existing within the intercostal space.

A generic device for creating an intercostal transcutaneous access to an operating field is known from U.S. Pat. No. 5,776,110 with the aid of which the intercostal space can be widened. This known device has a base body in the form of an oval flange to which a cylindrical sleeve to be inserted into an incision is attached in a distal direction, the diameter of which is greater than the intercostal space. Two opposing webs are formed on the distal end of the sleeve by means of flattenings on the sides of the sleeve by which the known device can be introduced into the intercostal space. The sleeve is turned about 90° over the oval base body to push the ribs apart, so that the distal webs touch the ribs and push these apart.

It is possible with this known device to increase the size of the intercostal space but it is disadvantageous that the sleeve always has to be turned through the full 90° due to its form and the arrangement of the webs, as a result the size of the intercostal space is not adjustable.

SUMMARY OF THE INVENTION

Based on this, the object of this invention is to create a device for creating an intercostal transcutaneous access to an operating field of the above-mentioned type which allows individual pushing apart of the ribs.

According to the invention, this object is achieved in that the at least two webs are mounted adjustable relative to each other on the base body.

The arrangement of the webs according to the invention as being movable relative to each other produces a variable adjustment range for pushing apart of the ribs and which can therefore be adapted to the respective requirements of the operation and/or the circumstances of the patient.

According to a practical embodiment of the invention it is suggested that the frame-shaped base body consists of two housing sections which can be adjusted relative to each other, wherein there is at least one web mounted on each housing section. This configuration is characterized by a simple design and thus also a construction which is simple to handle.

According to a preferred embodiment for designing the base body it is suggested that the two sections of the housing of the body are formed so as to be rotatable relative to each other about a vertical axis. For this embodiment both sections of the housing are, for example, formed as concentric rings which can easily be turned relative to each other.

The suggestion is furthermore made with the invention that an insert is insertable in the frame-shaped base body through which at least one medical instrument can be introduced into the operating field. Since endoscopic interventions in the thorax are often performed using an insufflation gas to increase the size of the operation chamber, this insert is advantageously attachable to the base body in such a way that the insert seals the operating field from the external environment. For example, to introduce the medical instruments the insert has membranes or the like sealed off access ports which also prevent escaping of the insufflation gas when a medical instrument is inserted.

According to a preferred embodiment of the invention on each housing section there are arranged two webs with each web preferably being pivotable about their longitudinal axis arranged on the respective housing section. The ability to rotate the webs always achieves optimal alignment of the webs relative to the ribs when using the device according to the invention. Use of respectively two webs per housing section is advantageous in order to allow even and secure pressing apart of the ribs.

Due to the arrangement of the webs on the respective housing section the webs span in each, the intercostal space spreading operating position of the webs a parallelogram-shaped plane between each other, forming an access to the operating field.

In order to seal the outer edge of the base body gas-tight against the incision it is proposed with a first embodiment of the invention, that a hose-shaped sleeve made out of an elastic material can be configured on the base body which surrounds the webs. This hose-shaped sleeve extends from the base body through the incision up to close to the distal end of the webs and is designed in such a way that it stretches elastically during movement apart of the webs to spread the ribs.

Optionally, this sleeve may include a feature such as a metallic loop at its distal end which may be inserted into the incision and has the effect of elastically opening the sleeve so that it is forced into contact with the walls of the incision, improving sealing.

According to an alternative embodiment of the sealing between the base body and the incision it is proposed according to the invention that a sealing element, preferably ring-shaped, which surrounds the incision is configurable on the base body and which touches the body of the patient, forming a seal against the patient's skin or the proximal part of the incision. The sealing may be enhanced by the use of a gel or viscous fluid applied to either surface.

In order to ensure that the device according to the invention cannot accidentally slip off the ribs when in the ribs spreading position or cannot be pulled out of the incision, it is proposed with the invention that each web has a projection at its distal end which essentially points at right angles to the outside to hook under a rib.

It is furthermore proposed according to the invention that every web has a flattened contact surface on the side adjacent to a rib in order to ensure secure and gentle placing of the webs against the ribs by ensuring that the contact area is large and the applied forces are widely distributed.

Operation of the device according to the invention can be simplified in that the two housing sections, and thus also the associated webs which push apart the ribs, can be locked in their relative position to each other, in particular by use of a locking mechanism. The locking mechanism is advantageously formed as a spring-loaded ratchet which can easily and quickly be released again by pressing a button.

Alternatively, a worm-wheel gear arrangement could be used to allow self-locking adjustment. A second alternative would be to fix a threaded bar between the handles, which may have its effective length adjusted by rotating an adjustment wheel.

In order to ensure that the device with the webs arranged on the distal side can be inserted forwards simply into the incision, it is proposed with the invention that all webs are essentially arranged in one line in the insert position in the intercostal space. The free distal end of each web is advantageously formed tapered in order to simplify insertion of the webs into the incision.

Each housing section advantageously has a handle sticking outwards to adjust the housing sections of the base body and therefore the moving apart of the webs.

Based on an alternative form for arrangement of the webs, it is proposed according to the invention that the webs are formed sharp at their distal end so that each can create an incision. For this embodiment the webs are not introduced through the central incision but self-sufficiently puncture the skin of the patient. Due to the flexibility of the skin the webs can be adjusted relative to each other to press apart the ribs through turning the housing sections of the base body. The actual incision is then subsequently formed within the frame-shaped base body. A port for minimally invasive surgery may be inserted into this incision, or it may be used for open surgery.

It is finally proposed with the invention that, according to an alternative embodiment for designing the base body, the two housing sections of the base body can be pivoted relative to each other about a horizontal axis.

Further features and advantages of the invention arise from the attached drawings in which three exemplary embodiments of a device according to the invention to create an intercostal transcutaneous access to an operating field are shown purely by way of example, without limiting the invention just to the exemplary embodiments shown. In the drawings:

BRIEF DESCRIPTION OF THE DRAWINGS

FIG. 5 shows a perspective view of a web;

FIG. 6 shows a procedure according to FIG. 1, but showing a second embodiment of the device according to the invention;

DETAILED DESCRIPTION OF THE INVENTION

Figure 1:
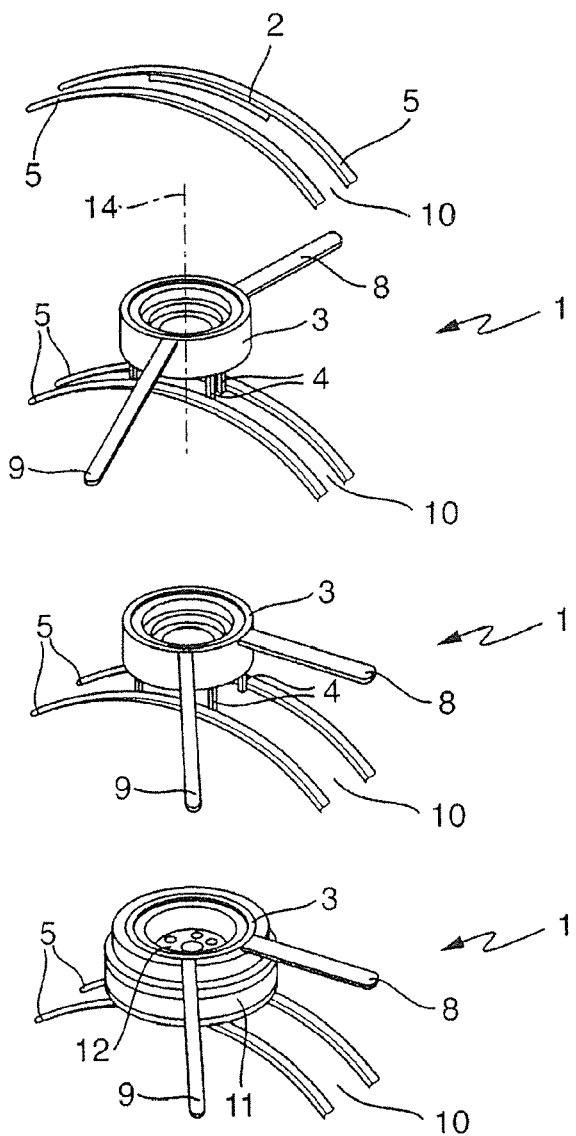
FIG. 1 shows a demonstration of a procedure for use of a device according to the invention according to a first embodiment.

In FIG. 1 is shown an exemplary schematic view of a device 1 for creating an intercostal transcutaneous access to an operating field as well as its use.

Figure 2:
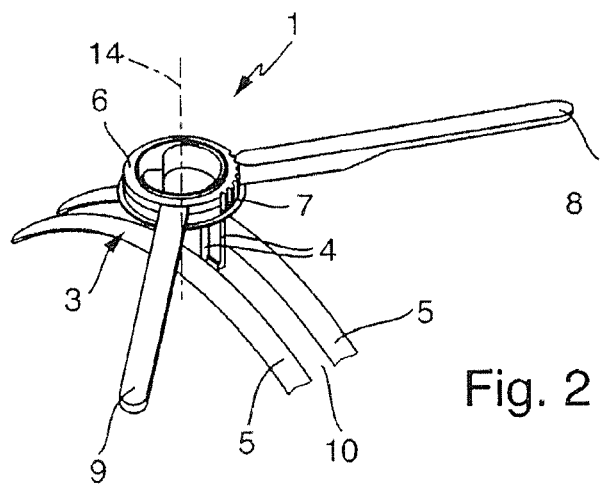
FIG. 2 shows a schematic perspective view of the device according to FIG. 1, showing the insertion position.
Figure 3:
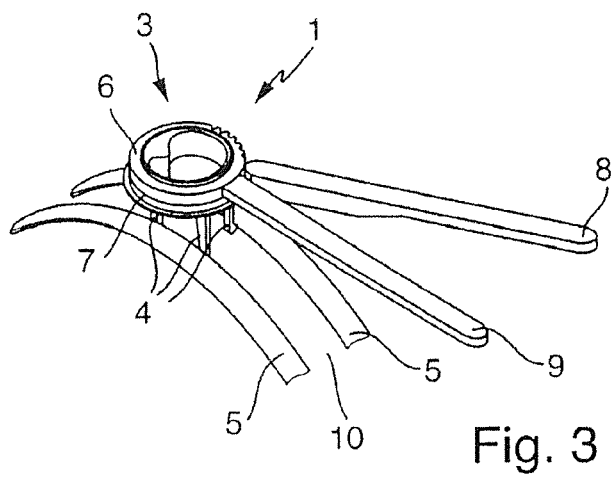
FIG. 3 shows a view according to FIG. 2, but showing a spreaded operating position.
Figure 4:
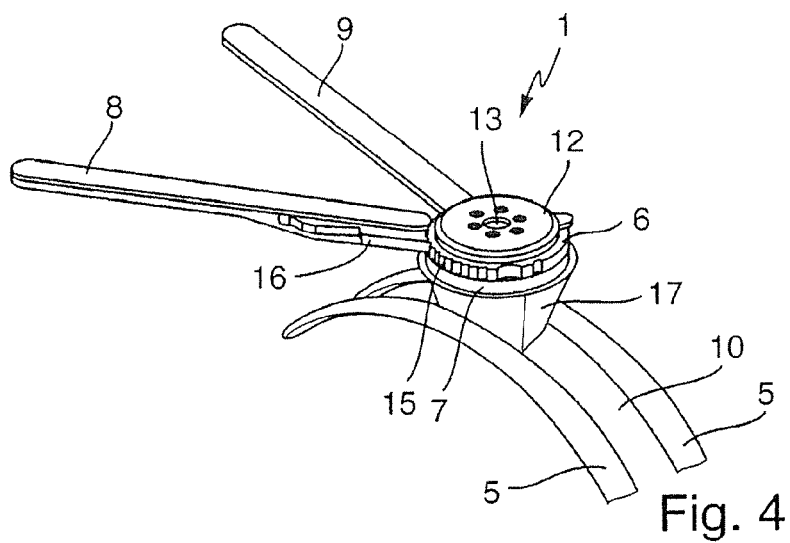
FIG. 4 shows a view according to FIG. 3, showing the whole device.
Figure 7:
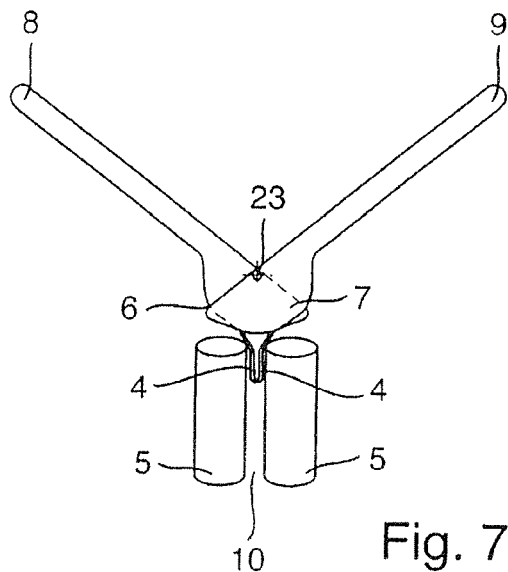
FIG. 7 shows a schematic side view of a third embodiment of a device according to the invention, showing the insertion position
Figure 8:
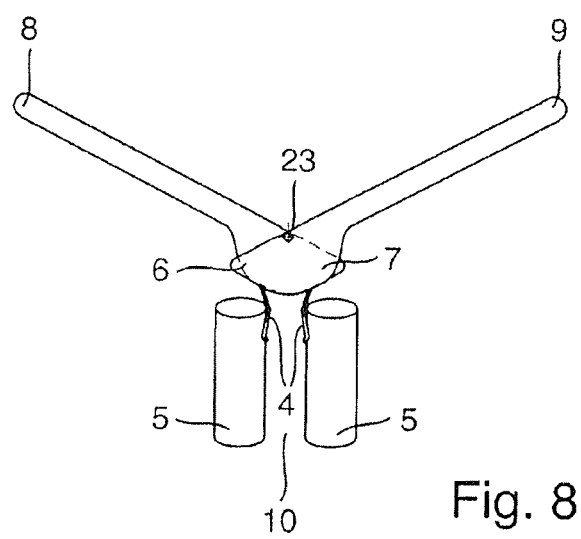
FIG. 8 shows a view according to FIG. 7, but showing a spreaded operating position.

The devices 1 shown in FIGS. 1 to 4 and FIGS. 6 to 8, the structure of which can best be seen in FIGS. 2 to 4 as well as FIGS. 7 and 8, essentially comprise an all-side frame-shaped base body 3 which closely surrounds an incision 2 on which the webs 4 are mounted on the distal side, over which two neighbouring ribs 5 of a patient can be pushed apart.

For the embodiments of the device 1 shown the base body 3 comprises two housing sections 6 and 7, wherein at least one web 4 is mounted on each housing section 6 and 7 and the housing sections 6 and 7 are designed to be adjustable relative to each other. Adjustment of both housing sections 6 and 7 of the base body 3 inevitably leads also to a relative adjustment of the webs 4 mounted on the housing sections 6 and 7, relative to each other.

Adjustment of both housing sections 6 and 7 relative to each other takes place over handles 8 and 9 sticking outwards from the housing sections 6 and 7.

Use of the device 1 according to FIG. 1 occurs as follows:

In a first step (the top-most figure) the surgeon creates the incision 2 intercostally, that is in an intercostal space 10. The device 1 with the webs 4 pointing forward is inserted into the incision 2, wherein the webs 4 are disposed in such a way in the inserted position (the second figure from above), that they are aligned in a straight line in order to allow simple and injury-free insertion of the webs 4 into the incision 2.

As can be seen from FIG. 1, for the embodiment of the device 1 shown the base body 3 has four webs 4 of which two are mounted on each housing section 6 and 7 of the base body, whereby the webs 4 of each housing section 6 and 7 are offset to each other by 180°.

Pressing together of the handles 8 and 9 causes the housing sections 6 and 7 to turn against each other, by which the webs 4 are also adjusted relative to each other, in this case away from each other. The webs 4 press the ribs 5 apart in this spreaded operating position (the third figure from above) of the webs 4 and thus increase the intercostal space 10.

Since an insufflation gas can also be used for endoscopic surgery in order to increase the size of the operation space, the outer edge of the base body 3 is, on the one hand, sealed against the patient in a final operating step (the lowest figure) and also, on the other hand, the free interior of the frame-shaped base body 3 which surrounds the incision 2 is sealed against the outer environment to prevent escaping of the insufflation gas.

The seal between the base body 3 and the incision 2 is achieved for the embodiments shown by a preferably ring-shaped sealing element 11 configurable on the base body 3 which surrounds the incision 2, which touches the body of the patient sealing up on the distal side.

Sealing of the free interior of the base body 3 which surrounds the incision 2 against the external environment takes place for this embodiment by an insert 12 which is insertable in the frame-shaped base body 3 through which at least one medical instrument can be introduced into the operating field. For example, to introduce the medical instruments the insert has membranes or the like sealed off access ports 13 which also prevent escaping of the insufflation gas when a medical instrument is inserted.

The exact structure of the device 1 according to FIG. 1 will now be described in more detail based on the following FIGS. 2 to 4.

As can be seen from FIGS. 2 to 4, the base body 3 for this first embodiment of a device 1 for creating an intercostal transcutaneous access to an operating field comprises two housing sections 6 and 7 formed as concentric rings which can be turned relative to each other about a vertical axis 14 by means of the handles 8 and 9. When pressing together the handles 8 and 9 the housing sections 6 and 7 are turned against each other in such a way that the webs 4 mounted on the housing sections 6 and 7 are moved apart starting from their alignment in a straight line in the insertion position, as can be seen in the sequence of FIGS. 2 and 3.

Due to the arrangement of the webs 4 on the respective housing section 6 and 7 the webs 4 span in each, the intercostal space 10 spreading operating position of the webs 4 a parallelogram-shaped plane between each other, forming an access to the operating field.

The webs 4 can be locked relative to each other in their respective spreaded position by means of a locking mechanism 15 on the base body 3 which is advantageously formed as a spring-loaded ratchet which can easily and quickly be released again by pressing a button 16.

In order to provide a better overview the FIGS. 2 and 3 show the device 1 without the components which are required to secure the device 1 gas-tight in the incision 2.

Figure FIG. 4 schematically shows the device 1 previously described on the basis of FIGS. 2 and 3 in a fully mounted and gas-tight condition disposed in the incision 2.

As already shown in FIG. 1 sealing of the free interior of the base body 3 which surrounds the incision 2 against the external environment takes place for this embodiment by means of an insert 12 which is insertable in the frame-shaped base body 3, through which at least one medical instrument can be introduced into the operating field.

The gas-tight sealing of the outer edge of the base body 3 against the incision 2 takes place for this embodiment by means of a hose-shaped sleeve 17 made out of an elastic material which can be configured on the base body 3 surrounding the webs 4. This hose-shaped sleeve 17 extends from the base body 3 through the incision 2 upwards almost to the distal end of the webs 4 and is designed in such a way that it stretches elastically during movement apart of the webs 2 to spread the ribs 5.

Figure FIG. 5 shows in a perspective view an exemplary structure of a web 4 used to press apart the ribs 5. All of the webs 4 mounted on the base body 3 are advantageously configured identical in order to simplify their manufacture and assembly.

All webs 4 are pivotable about their longitudinal axis 18 mounted on the associated housing sections 6 and 7 of the base body 3, in order to achieve, as gentle as possible and at the same time, an appropriately selected placing of the webs 4 on the ribs 5. In order to ensure that the device 1 cannot accidentally slip off the ribs 5 when in the ribs 5 spreading position or can be pulled out of the incision 2, the webs 2 have a projection 19 at their distal end which essentially points at right angles to the outside to hook under the respective rib 5.

It is furthermore clear from FIG. 5 that every web 4 has a flattened contact surface 20 on the side adjacent to a rib 5 in order to ensure secure and gentle placing of the web 4 against the rib 5.

To simplify insertion of the webs 4 into the incision 2 and to avoid causing injuries, the free distal ends 21 of the webs 4 are advantageously formed tapered.

The groove 22 shown in FIG. 5, formed at the distal end 21 of the web 4, serves to secure the hose-shaped sleeve 17 which in turn serves to seal the incision 2, surrounding the webs 4 and being fixable on the base body 3. For securing the hose-shaped sleeve 17 there is a circumferential bulge formed both at the proximal end and distal end of the sleeve 17 which is configurable in the respective mounts on the base body 3 and on the webs 4, namely the groove 22.

The FIGS. 6 to 8 show two alternative embodiments for creating an a device 1 for creating an intercostal transcutaneous access to an operating field.

The procedure shown in FIG. 6, as well as the second embodiment of a device 1 shown in FIG. 6, essentially differs from the procedure and the first embodiment of the device 1 according FIG. 1 in that the distal ends 21 of the webs 4 for this device 1 are made sharp for each to create an own incision. This means that for this embodiment the webs 4 are not inserted through a previously formed central incision 2 in the patient's body, but that the webs 4 each self-sufficiently puncture the skin of the patient. Due to the flexibility of the skin the webs 4 can be adjusted afterwards relative to each other to press apart the ribs 5 by turning housing sections 6 and 7 of the base body 3 relative to each other. The actual incision 2 is then subsequently formed within the frame-shaped base body 3.

Gas-tight sealing of the base body 3 against the outer side of the base body 3 can again take place for this embodiment by means of the sealing element 11 already described above with FIG. 1, which is fixable on the base body 3 and surrounds the incision 2, preferably in the form of a ring, and which touches the body of the patient and sealing up on the distal side.

Sealing of the free interior of the base body 3 which surrounds the incision 2 against the external environment takes place by means of the insert 12 which was already described with FIG. 1, which is insertable in the frame-shaped base body 3 and through which at least one medical instrument can be introduced into the operating field.

The third embodiment shown in FIGS. 7 and 8 to create the device 1 essentially differs from both of the previously described embodiments in that the two housing sections 6 and 7 which form the base body 3 are pivotable about a horizontal axis 23 relative to each other.

For the embodiment shown, each housing section 6 and 7 of the base body 3 has only one web 4, which extends over the whole width of the base body 3. When pressing apart, the handles 8 and 9 shown in FIG. 8 the housing sections 6 and 7 are pivoted against each other about the horizontal axis 23 by means of which the webs 4 firmly connected to the housing sections 6 and 7 are pressed outwards thereby pressing the ribs 5 apart and increasing the intercostal space 10.

The devices 1 described above formed to create an intercostal transcutaneous access to an operating field are characterized in that the webs 4 are adjustable relative to each other which means that the size of intercostal space 10 can be varied and therefore an adjustable adjustment range for pressing apart the ribs 5 is possible to adapt to the respective requirements of the operation and/or the circumstances of the patient.

What is claimed is:

1. A device for creating an intercostal transcutaneous access to an endoscopic operating field, the device comprising:

an all-side frame-shaped base body configured to closely surround an incision; and at least four webs mounted on the base body and configured to be introduced into an intercostal space so that two ribs of a patient arranged next to each other can be moved apart;

wherein the at least four webs are mounted adjustable relative to each other on the base body between an insertion position and an operating position, wherein the base body includes two housing sections which are formed to be rotatable relative to each other about a vertical axis and wherein there are at least two webs mounted on a distal side of each housing section, wherein in the insertion position the at least four webs of the base body are aligned in a straight line.

2. The device according to claim 1, wherein an insert is insertable in the frame-shaped base body through which at least one medical instrument can be introduced into the operating field.

3. The device according to claim 2, wherein the insert is configurable on the base body to seal the operating field from the external environment.

4. The device according to claim 1, wherein the webs are each pivotable about their longitudinal axis arranged on the respective housing section.

5. The device according to claim 1, wherein the webs are configured to span in each the intercostal space spreading operating position of the webs a parallelogram-shaped plane between each other.

6. The device according to claim 1, wherein a hose-shaped sleeve made out of an elastic material can be configured on the base body surrounding the webs.

7. The device according to claim 1, wherein a sealing element, preferably ring-shaped, which surrounds the incision is configurable on the base body.

8. The device according to claim 1, wherein each web has a projection at its distal end which essentially points at right angles to the outside to hook under a rib.

9. The device according to claim 1, wherein every web has a flattened contact surface on the side adjacent to a rib.

10. The device according to claim 1, wherein the two housing sections can be locked in their relative position to each other by means of a locking mechanism.

11. The device according to claim 1, wherein all webs are configured to be arranged in the insert position in the intercostal space essentially in one line.

12. The device according to claim 1, wherein each housing section has a handle sticking outwards by means of which the housing sections are adjustable relative to each other.

13. The device according to claim 1, wherein the webs are formed sharp at their distal end so that each can create an incision.

14. The device according to claim 1, wherein the two housing sections are formed so as to be pivotable relative to each other about a horizontal axis.

* * * * *